US008545831B2

(12) United States Patent
Roy et al.

(10) Patent No.: US 8,545,831 B2
(45) Date of Patent: Oct. 1, 2013

(54) COMPOSITIONS AND METHODS FOR TREATING A DAMAGED CARDIOVASCULAR ELEMENT

(75) Inventors: Josee Roy, Memphis, TN (US); Hezi-Yamit Ayala, Windsor, CA (US); Carol Sullivan, Fairfax, CA (US); Mingfei Chen, Santa Rosa, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1356 days.

(21) Appl. No.: 11/443,594

(22) Filed: May 31, 2006

(65) Prior Publication Data
US 2007/0012323 A1    Jan. 18, 2007

Related U.S. Application Data

(60) Provisional application No. 60/685,831, filed on May 31, 2005.

(51) Int. Cl.
*A61K 31/77* (2006.01)
(52) U.S. Cl.
USPC ........................................................ 424/78.38
(58) Field of Classification Search
None
See application file for complete search history.

(56) References Cited

U.S. PATENT DOCUMENTS

| | | | | |
|---|---|---|---|---|
| 4,938,763 | A * | 7/1990 | Dunn et al. | 604/891.1 |
| 5,776,097 | A * | 7/1998 | Massoud | 604/500 |
| 6,290,729 | B1 * | 9/2001 | Slepian et al. | 623/23.72 |
| 7,582,680 | B1 | 9/2009 | Shi et al. | |
| 7,837,987 | B2 | 11/2010 | Shi et al. | |
| 2003/0118545 | A1 | 6/2003 | Shi et al. | |
| 2005/0069520 | A1 | 3/2005 | Shi et al. | |
| 2006/0280718 | A1 | 12/2006 | Roy et al. | |
| 2007/0237740 | A1 * | 10/2007 | Reddington et al. | 424/78.08 |

FOREIGN PATENT DOCUMENTS

WO        02092107        11/2002

OTHER PUBLICATIONS

Diaz et al, Antioxidants and Atherosclerotic Heart Disease, The New England Journal of Medicine, 1997, 337(6), 408-416.*

Thierry Hauet, et al., "Protective Effect of Polyethylene Glycol against Prolonged Cold Ischemia and Reperfusion Injury: Study in the Isolated Perfused Rat Kidney," The Journal of Pharmacology and Experimental Therapeutics, vol. 297(3),p. 946-952, (Mar. 23, 2001).
Yee Ling Leung, et al., "Cord Monitoring Changes and Segmental Vessel Ligation in the "At Risk" Cord During Anterior Spinal Deformity Surgery," SPINE, vol. 30(16),p. 1870-1874, (2005).
Gary Davidoff, et al., "Function-limiting Dysethetic Pain Syndrome Among Traumatic Spinal Cord Injury Patients: a Cross-sectional Study," Pain, Elsevier Science Publishers B.V. , 29: p. 39-48, (1987).
Aleksandar Berie, "Post-Spinal Cord Injury Pain States," Pain, Elsevier Science B.V., 72: p. 295-298, (Mar. 23, 1997).
Nanna B. Finnerup, M.D., "Intravenous Lidocaine Relieves Spinal Cord Injury Pain," Anesthesiology, 102:p. 1023-30, (2005).
Kwon, et al. "Magnesium Chloride in a Polyethylene Glycol Formulation as a Neuroprotective Therapy for Acute Spinal Cord Injury: Preclinical Refinement and Optimization," Journal of Neurotrauma 26, 1379-1393 (Aug. 2009).
Kwon, et al. "A Grading System to Evaluate Objectively the Strength of Pre-Clinical Data of Acute Neuroprotective Therapies for Clinical Translation in Spinal Cord Injury," Journal of Neurotrauma, 28, 1525-1543 (Aug. 2011).
Kwon, et al. "Translational Research in Spinal Cord Injury: A Survey of Opinion from the SCI Community," Journal of Neurotrauma, 27, pp. 21-33 (Jan. 2010).
McKee, et al. "Analysis of the Brain Bioavailability of Peripherally Administered Magnesium Sulfate: A Study in Humans with Acute Brain Injury Undergoing Prolonged Induced Hypermagnesemia," Crit. Care Med., 33(3), 661-666 (Mar. 2005).
Journal of Spinal Cord Medicine, 34(6), 620-621 (2011).

* cited by examiner

*Primary Examiner* — Paul Dickinson
(74) *Attorney, Agent, or Firm* — William D. Schmidt; Sorell, Lenna & Schmidt, LLP

(57) ABSTRACT

In the present invention, the applicants describe methods and compositions of treating damaged cardiovascular elements and cardiovascular conditions including hypotension, atherosclerotic lesions, vulnerable plaque, and acute myocardial infarct. The applicants demonstrate the ability of a biomembrane sealing agent to accumulate on the walls of damaged blood vessels and help improving mean arterial pressure following tissue injury. The applicants describe the use of formulations comprising at least one biomembrane sealing agent and one bioactive agent for prophylactic treatment such as they could be administered concurrently to an invasive therapeutic intervention or after the insult (i.e. post-injury or post-surgery). Alternatively, these methods and compositions could be used to reduce the severity of cardiovascular diseases after onset.

23 Claims, No Drawings

COMPOSITIONS AND METHODS FOR TREATING A DAMAGED CARDIOVASCULAR ELEMENT

CROSS REFERENCE TO RELATED APPLICATIONS

This application claims the benefit of provisional application No. 60/685,831, filed on May 31, 2005, which is incorporated herein by reference.

FIELD OF THE INVENTION

This invention relates to methods and compositions to treat damaged cardiovascular elements and improve blood flow.

BACKGROUND

Pain is associated with a myriad of medical conditions and affects millions of Americans. As reported by the American Pain Foundation, over 50 million Americans suffer from chronic pain including 20% of individual aged 60 and over who are affected by joint (arthritis or other disorders) and back pain. Furthermore, nearly 25 millions Americans experience acute pain due to injuries or surgical procedures each year. The cost involved in the management of pain has been estimated at $100 billion each year. In addition to its economical burden, pain has a tremendous effect on the quality of life of affected individuals and is one of the most common causes of disability.

Accordingly, improved methods and compositions of treating acute and chronic pain are desired to alleviate these debilitating conditions.

Conditions affecting cardiovascular functions and blood flow have increased substantially in countries of central and eastern Europe and remains the major cause of premature death in Western populations. For example, atherosclerosis which involves formation of depots or plaque into arteries, caused almost 1 million deaths in 1992—twice as many as from cancer and 10 times as many as from accidents. Despite significant medical advances, coronary artery disease (which results from atherosclerosis and causes heart attacks) and atherosclerotic stroke are responsible for more deaths than all other causes combined.

Accordingly, there is an urgent need for improved methods and compositions for treating conditions affecting cardiovascular elements and blood flow.

SUMMARY OF THE INVENTION

The current invention fulfills this and other foregoing needs by providing devices, methods, and compositions useful for treating or preventing pain consisting of at least one biomembrane sealing agent.

In addition, improved methods and compositions of treating damaged cardiovascular elements are desired.

The instant invention fulfills this and the other foregoing needs by providing improved compositions and methods for treatment of conditions associated with acute and chronic pain as well as conditions associated with damaged cardiovascular elements and impaired blood flow.

In one aspect, the present invention provides a composition for treating a pathological condition associated with acute or chronic pain as well as damaged cardiovascular elements comprising at least one biomembrane sealing agent. In one embodiment, the at least one biomembrane sealing agent is delivered in an injectable formulation. In another embodiment, the at least one biomembrane sealing agent comprises more than 10% of the injectable formulation. In another embodiment of the invention, the composition is incapable of forming a gel.

In different embodiments of the invention, the at least one biomembrane sealing agent is selected from the group consisting of polyoxyethylenes, polyalkylene glycol, poly (ethylene glycol) or PEG, polyvinyl alcohol, pluronics, poloxamers, methyl cellulose, sodium carboxylmethyl cellulose, hydroxyethyl starch, polyvinyl pyrrolidine, dextrans, poloxamer P-188, poly(polyethylene glycol methacryalte), poly(glycerol methacrylate), poly(glycerol acrylatete), poly(polyethylene glycol acrylate), poly(alkyl oxazoline), phosphoryl choline polymers, sodium and potassium polymethacrylate, sodium and potassium polyacrylate, polymethacrylatic acid and polyacrylic acid and any combinations thereof.

In yet another aspect, the invention provides a method of treating a pathological condition associated with pain or damaged cardiovascular elements, the method comprising delivering to a subject in need thereof a therapeutically effective amount of at least one biomembrane sealing agent, In one embodiment, the at least one biomembrane sealing agent is delivered in an injectable formulation. In another embodiment, the at least one biomembrane sealing agent comprises more than 10% of the injectable formulation. In one embodiment of the invention, the composition is incapable of forming a gel.

In yet another aspect, the invention provides that a biomembrane sealing agent, such as, for example, PEG, may also potentiate the beneficial effects of bioactive agents. In different embodiments, such bioactive agents include, neurotransmitter and receptor modulators, anti-inflammatory agents, antioxidants, anti-apoptotic agents, nootropic and growth agents; modulators of lipid formation and transport, antiplatelet and anticoagulant agents, antineoplastic agents and agents that interfere with cellular division, blood flow modulators and any combinations thereof.

Further, in different embodiments, the at least one biomembrane sealing agent and the at least one bioactive agent may be delivered by a method selected from the group consisting of an intravenous administration, an intramuscular administration, an intrathecal administration, a subcutaneous administration, an intra-articular administration, an epidural administration, a parenteral administration, a direct application onto a site of the pathological condition, an implanted depot, and any combinations thereof. Certain aspects of the present invention provides for modes of vascular delivery such as perivascular, transvascular or catheter local delivery using applicable catheter controlled from a stent.

Preferably, biomembrane sealing agent(s) can be used to treat various clinical conditions showing a chronic pain component including metabolic neuropathies such as diabetic and alcoholic neuropathies, postherapeutic neuralgia, Complex Regional Pain Syndrome and other pain syndromes derived from trauma to the central nervous system such as stroke, traumatic brain or spinal cord injury, pain derived from mechanical or biochemical neuronal insults such as discogenic pain, sciatica, carpal tunnel syndrome, phantom limb pain and pain associated with degenerative conditions such as multiple sclerosis, arthritis and other joint diseases.

Another aspect of the present invention provides for treatment of acute pain associated with damaged or inflamed tissue derived from a traumatic insult or derived from surgical and invasive therapeutic interventions.

Certain aspects of the present invention provide for treatment of cardiovascular indications, such as for example, atherosclerotic lesions, vulnerable plaque, and acute myocardial infarct.

One aspect of the present invention provides for biosealing of the atherosclerotic lesions. This aspect of the present invention may also provides for a combination of a biosealing agent and anti-inflammatory agent.

Another aspect of the present invention provides for biosealing of the plaque area to reduce thrombogenicity (platelets deposition).

Another aspect of the present invention provides for biosealing during and after aMI to reduce injury and oxidation related damage.

In one aspect, the invention provides a composition useful for treating or preventing pain consisting of at least one biomembrane sealing agent, wherein the at least one biomembrane sealing agent is selected from the group consisting of poly (ethylene glycol), a block copolymer containing a polyalkylene glycol, triblock containing a polyalkylene glycol, a block copolymer containing a polyalkylene oxide, triblock containing a polyalkylene oxide, polyvinyl alcohol, polyvinyl pyrrolidone, dextrans, poloxamine, pluronic polyols, dimethylsulfoxide, hydroxyethylstarch, sodium carboxymethyl cellulose, poly(polyethylene glycol methacryalte), poly (glycerol methacrylate), poly(glycerol acrylatete), poly (polyethylene glycol acrylate), poly(alkyl oxazoline), phosphoryl choline polymers, sodium and potassium polymethacrylate, sodium and potassium polyacrylate, polymethacrylatic acid and polyacrylic acid and combinations thereof.

In one embodiment of the invention, the at least one biomembrane sealing agent is poly (ethylene glycol).

In another aspect, the invention provides a composition of useful for treating or preventing pain consisting of at least one biomembrane sealing agent, wherein the at least one biomembrane sealing agent is PEG molecules having a molecular weight of between about 1,400 and about 20,000 Da.

In one embodiment of the invention, the at least one biomembrane sealing agent has a linear or muti-arm structure.

In another aspect, the invention provides a method for treating or preventing pain comprising administering to a subject an effective amount of at least one biomembrane sealing agent(s) by parenteral administration, intravenous, subcutaneous, intramuscular, intra-articular, intrathecal and epidural administration.

In another aspect, the invention provides a method of preventing pain in a subject comprising administering post-injury, concurrently or after surgery or therapeutic intervention, but before the onset of acute or chronic pain, an effective amount of at least one biomembrane sealing agent.

In another aspect, the invention provides a method for reducing the severity of the symptoms after onset of acute or chronic pain in a subject comprising administering to a subject suffering from the onset of pain an effective amount of a biomembrane sealing agent(s) by parenteral administration, intravenous, subcutaneous, intramuscular, intra-articular, intrathecal and epidural administration.

In one aspect, the invention provides a method for reducing the severity of the symptoms after onset of chronic pain in a subject, wherein the subject is suffering from diabetic neuropathy, alcoholic neuropathies, postherapeutic neuralgia, Complex Regional Pain Syndrome, stroke, traumatic brain injury, spinal cord injury, discogenic pain, sciatica, carpal tunnel syndrome, phantom limb pain, multiple sclerosis, arthritis and other joint diseases In one aspect, the invention provides a method for reducing the severity of the symptoms after onset of acute pain derived from a traumatic insult or derived from surgical and invasive therapeutic interventions.

In one aspect, the invention provides a composition for treating or preventing pain consisting essentially of at least one biomembrane sealing agent.

In one embodiment, the invention provides a composition for treating or preventing pain consisting essentially of at least one biomembrane sealing agent, wherein the at least one biomembrane sealing agent is polyethylene glycol.

In another embodiment, the invention provides a composition for treating or preventing pain consisting essentially of at least one biomembrane sealing agent, wherein at least two biomembrane sealing agents are administered.

In another embodiment, the invention provides a composition for treating or preventing pain consisting essentially of at least one biomembrane sealing agent, wherein said at least two biomembrane sealing agents are administered simultaneously or sequentially.

In another embodiment, the invention provides a composition for treating or preventing pain consisting essentially of at least one biomembrane sealing agent, wherein the administration is repeated.

DETAILED DESCRIPTION

In the present invention, the applicants describe the effect of a biomembrane sealing agent, poly(ethylene glycol), on the development of chronic pain following tissue injury as well as acute pain in a model of acute inflammation. The applicants demonstrated the ability of this class of agents referred to as "biomembrane sealing agents" to reduce the severity of hyperalgesia and/or allodynia following mechanical and chemical tissue injuries. The applicants show the ability of a biomembrane sealing agent to accumulate on the walls of damaged blood vessels and help restoring normal blood flow and mean arterial pressure in injured animals. The applicants describe the use of injectable formulations of biomembrane sealing agent(s) for prophylactic treatment such as they could be administered concurrently to an invasive therapeutic intervention or after the insult (i.e. post-injury or post-surgery) but before the onset of acute or chronic pain or cardiovascular disease. Alternatively, biomembrane sealing agents could be used to reduce the severity of symptomatic pathological pain and cardiovascular disease after onset.

To aid in the understanding of the invention, the following non-limiting definitions are provided:

The term "treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols which have only a marginal effect on the patient.

The term "subject" includes a living or cultured system upon which the methods and/or kits of the current invention is used. The term includes, without limitation, humans.

The term "practitioner" means a person who practices methods, kits, and compositions of the instant invention on the subject. The term includes, without limitations, doctors, other medical personnel, and researchers.

Allodynia and hyperalgesia are terms used to define pain symptoms and the extent of the body region affected by pain.

Accordingly, the term "allodynia" refers to pain resulting from a stimulus that ordinarily does not elicit a painful response.

The term "hyperalgesia" refers to an increased sensitivity to a normally painful stimulus. Primary hyperalgesia affects the immediate area of the injury.

The term "acute pain" refers to pain resulting from an acute event and generally decreasing in intensity over a period of a few days to a few weeks.

The term "chronic pain" refers to pain resulting from an acute or repeated events and generally increasing in intensity over a period of a few weeks to years.

The term "damaged" refers to a condition derived from acute or repetitive insults including without limitation, mechanical, chemical and biological insults such as inflammation and pathological deposition of biological materials and free radicals.

The term "cardiovascular elements" refer to the heart and blood vessels including arteries, veins and capillaries.

The term "bioactive agent" refers to chemical compounds and biological compounds including protein, peptide, polypeptide, antibody, antibody fragment, DNA, RNA and cell.

All references to chemical compounds, including without limitation, biomembrane sealing agents, markers, and bioactive agents include all forms of these chemical compounds (i.e., salts, esters, hydrates, ethanolates, etc.), wherein said forms possess at least partial activities of the respective chemical compounds.

Acute and Chronic Pain Indications

There are two basic forms of physical pain: acute and chronic. Acute pain, for the most part, results from disease, inflammation, or injury to tissues. It is mediated by activation of sensory fibers also known as nociceptive neurons. Nociceptive pain normally disappears after healing, for example in cases of post-traumatic or post-operative pain. Unfortunately, in some individuals, pathological changes occur that increase the sensitivity of the sensory neurons. In those cases, symptomatic pain can become chronic and persists for months or even years after the initial insult.

Acute insults of mechanical, chemical or biological nature can trigger the development of chronic pain. It may also derive from various chronic conditions linked to persistent on-going tissue damage due, for example, to chronic inflammatory reactions or autoimmune diseases.

Pain and the extent of the area affected by pain can be defined by the measure of allodynia and hyperalgesia. Allodynia is defined as pain resulting from a stimulus that ordinarily does not elicit a painful response. Hyperalgesia is defined as an increased sensitivity to a normally painful stimulus. Primary hyperalgesia affects the immediate area of the injury. The term secondary hyperalgesia or referred pain is normally utilized in cases when sensitization has extended to a broader area surrounding the injury.

There are two main modalities of pain: visceral for internal organs and somatic for peripheral tissues. Somatic sensations are relayed from the periphery to the central nervous system by the A and C sensory fibers which have their nucleus in the dorsal root ganglia lining the spine. At one extremity, these neurons have receptors, called "nociceptors", buried in tissues that can respond to various stimuli including pressure, temperature and pH. These fibers act as transducers, converting stimuli into nociceptive impulses that are promptly transmitted to the projection neurons located in the spinal cord. These projections neurons will then transmit the sensory signals to the brain via brainstem, thalamic and other supraspinal structures before the signals finally reach the corticocerebral sensory areas.

The perception and relay of painful sensations carried by neuronal fibers can be modulated at various levels including peripheral endings, intermediate levels such as in the spinal cord, brainstem, thalamic and other supraspinal structures or even in the cerebral cortex. Increased sensory information and translation to pain can be achieved by direct mechanisms such as increased number of sensory endings and expression and/or increased sensitivity of their receptors. Relay of the sensory information to the brain can also be regulated directly or indirectly by interneurons, ascending and/or descending neuronal fibers. Inflammation, disturbance of blood flow and/or changes in the characteristics of the blood-CNS-barrier can influence the occurrence and/or severity of acute and chronic pain.

Clinically, these changes may manifest as an increased response to a noxious stimulus (hyperalgesia), a painful response to a normally innocuous stimulus (allodynia), prolonged pain after a transient stimulus (persistent pain), and/or the spread of pain to uninjured tissue (i.e., referred pain).

Chronic pain etiologies include radiculopathy, plexopathy, peripheral nerve lesion, Complex Regional Pain Syndrome and central pain. Examples of clinical conditions associated with chronic pain include metabolic neuropathies such as diabetic and alcoholic neuropathies, postherapeutic neuralgia, pain syndromes derived from trauma to the central nervous system such as stroke, traumatic brain, spinal cord or caudal equine injuries, pain derived from mechanical or biochemical neuronal insults such as discogenic pain, sciatica, carpal tunnel syndrome, phantom limb pain and symptomatic pain associated with degenerative conditions such as multiple sclerosis, arthritis and other joint diseases.

Additional clinical conditions would include acute or chronic symptomatic pain derived from surgical or other invasive interventions as well as acute or chronic pain derived from injury of peripheral neuronal or non-neuronal tissues.

Inflammation is the body's normal protective response to conditions that include a tissue necrosis component. Tissue necrosis can be derived from a mechanical, chemical, biological or biochemical insult. Clinical conditions with an inflammatory component include traumatic tissue injury, surgery, invasive therapeutic intervention, degenerative diseases such as arthritis and other joint diseases as well as irritation, hypersensitivity, and auto-immune reactions.

During this natural "defense" process, local increases in blood flow and capillary permeability lead to accumulation of fluid, proteins and immune cells in the inflamed area. Some of these cells can release chemical mediators of inflammation including histamine, cytokines, bradykinin and prostaglandins that can attract more immune cells at the site of inflammation and/or increase the sensitivity of pain fibers within the affected area. As the body mounts this protective response, the symptoms of inflammation develop. These symptoms include, without limitation, pain, swelling and increased warmth and redness of the skin. The inflammatory response has to be tightly regulated otherwise it may lead to tissue necrosis and development of acute and chronic pain conditions.

Exemplary pro-inflammatory molecules include cytokines, chemokines, neuropeptides, bradykinin, histamine and prostaglandins. Suitable active ingredients may include steroids, nonsteroidal anti-inflammatory drugs, COX inhibitors, modulators of TNF-alpha or IL-1 cytokine levels or receptors.

It appears that there is no direct and positive correlation between increased or the level of preserved neuronal activity after tissue injury and decreased incidence of chronic pain development. To the contrary, studies have reported an inverse association between the severity of neuronal insults and the development of chronic pain syndromes. For example, posttraumatic headaches are more common in mild cases of brain injury as compared to severe and moderate cases of brain injury. Similarly, in the population affected by spine injury, an increased risk of developing chronic pain has been associated with milder conditions relative to more severely impaired cases (Nepomuceno et al., 1979, Davidoff et al., 1987: Demirel et al., 1998). In those studies, the incidence of the development of chronic pain was higher in paraplegic versus tetraplegic patients, and in patients with incomplete versus those with complete spinal cord lesions. Furthermore, it appears that within the complete population, only individuals with some measurable transmission across the spinal lesion may experience pain below the injury whereas a majority of patients without pain had no residual neuronal function below the site of lesion (Beric, 1997). In those conditions, a therapy that can increase recovery of neuronal activity following direct or indirect injury to the nervous system would not be indicative of a potential reduction in the occurrence or severity of pathological pain in those patients.

Patients with symptomatic pain from a broad range of etiologies are affected by acute or chronic allodynia and hyperalgesia. Specific scoring systems have been developed to monitor changes in sensitivity to painful (hyperalgesia) or normally nonpainful (allodynia) stimuli. These Quantitative Sensory Tests (QST) are becoming the new method of choice in assessing evoked pain in patients with pain syndromes. QST have been utilized to test various drugs for patients who developed acute or chronic pain symptoms following insults to central and/or peripheral neuronal components including SCI and stroke (Attal et al., 2000; Attal et al., 2002; Finnerup et al., 2005), surgeries or other invasive treatments, injuries such as bone fractures, shingles and development of postherapeutic neuralgia (Leung et al., 2001), phantom limb pain and idiopathic neuropathy (Attal et al., 1998).

Scoring systems to monitor acute and chronic allodynia and hyperalgesia in animal models of tissue injury have been used extensively to study the mechanisms involved in the sensation of pain and to test potential treatments. More recently, similar scoring systems have been applied to pain syndromes that can be developed after injury to the central nervous system (Gris et al., 2004; Hao et al., 2004).

In both humans and animals, tissue injuries such as high thoracic and cervical spinal cord injury often result in hypotension or reduced mean arterial pressure at rest which reduces tissue perfusion and may impair functional recovery and orthostatic tolerance.

Autonomic dysreflexia is also a common and potentially life threatening condition associated with spine injury, characterized by large increases in blood pressure in response to a stimuli below the level of injury; most commonly bladder or bowel distension.

Biomembrane Sealing Agents

For more than 40 years, biomembrane sealing agents of various molecular weights have been utilized as adjuncts to culture media for their ability to protect cells against fluid-mechanical injuries. These agents include hydrophilic polymers such as polyoxyethylenes, polyalkylene glycol, polyethylene glycols (PEG), polyvinyl alcohol, amphipatic polymers such as pluronics or poloxamers, including poloxamer P-188 (also known as CRL-5861, available from CytRx Corp., Los Angeles, Calif.) (Michaels and Papoutsakis, 1991) as well as methyl cellulose (Kuchler et al., 1960), sodium carboxylmethyl cellulose, hydroxyethyl starch, polyvinyl pyrrolidine and dextrans (Mizrahi and Moore, 1970; Mizrahi, 1975; Mizrahi, 1983).

Some biomembrane sealing agents including hydroxyethyl starch (Badet et al., 2005) and PEG (Faure J. P., et al., (2002) *Polyethylene glycol reduces early and long-term cold ischemia-reperfusion and renal medulla injury. J Pharmacol Exp Ther* September; 302(3):861-70; Hauet et al., 2001) have shown effective cryopreservative abilities in organ transplantation studies. Poloxamer P-188 and a neutral dextran protected muscle cells against electroporation or thermally driven cell membrane permeabilization (Lee et al., 1992). Direct application of PEG was shown to increase neuronal activity of transected or crushed axon (Bittner et al., 1986), peripheral nerve (Donaldson et al., 2002) and spinal cord preparations in vitro (Lore et al., 1999; Shi et al., 1999; Shi and Borgens, 1999; Shi and Borgens, 2000; Luo et al., 2002) or in vivo (Borgens et al., 2002). Intravenous or subcutaneous administration of PEG or Poloxamer P-188 increased the cutaneous trunchi muscle reflex response after experimental spinal cord contusion in guinea pigs (Borgens and Bohnert, 2001; Borgens et al., 2004) and increased neuronal activity in a naturally occurring spinal cord injury model in dogs (Layerty et al., 2004). PEGs of various molecular weights from 1,400-20000 Da, having a linear or multiple arms structure were shown to increase neuronal activity following tissue injury (Hauet et al., 2001; Detloff et al., 2005; Shi et al., 1999).

Biomembrane sealing agents can be effective following different modes of delivery including local and prolonged cellular exposure, direct and short-term tissue or organ exposure or systemic administration. Effective concentrations of biomembrane sealing agents may vary depending on the purpose and/or mode of delivery For example, about 0.05% concentration is effective in tissue culture applications (Michaels and Papoutsakis, 1991) and about 30% to about 50% concentration is effective for organ preservation and upon in vivo administration in animals (Hauet et al., 2001; Shi et al., 1999; Borgens and Bohnert, 2001; Borgens et al., 2004).

As mentioned earlier, it appears that there is no direct and positive correlation between increased or the level of preserved neuronal activity after tissue injury and decreased incidence of chronic pain development. For example, milder injuries have been associated with increased incidence of chronic pain in SCI and TBI patients (Lahz and Byrant, 1996; Uomoto and Esselman, 1993; Beetar et al., 1996; Nepomuceno et al., 1979, Davidoff et al., 1987: Demirel et al., 1998). Furthermore, it has been suggested that in SCI patients, a certain level of neuronal functions across the spinal lesion is a prerequisite for development of chronic pain at level or below the lesion (Beric, 1997).

In clinical settings, the acute and sub-acute intervention in cases of injury to the nervous system is directed toward maintaining the patient alive in cases of life-threatening injury and to the preservation of neuronal functions in general. In other words, the "state of care" will be focusing on the amount of sensory, motor and cognitive functions that are recovered following injury and during the rehabilitation program. Less emphasis will be applied to monitoring the occurrence of pathological dysfunction in the newly recovered neuronal activity. The main reason for that is probably that these pathological dysfunctions do not manifest clearly before most patients have left the rehabilitation center. For example, a majority of SCI clinical trials have used the ASIA score to evaluate the effect of acute treatments or drugs delivered. The ASIA score has been conceived to monitor sensory and motor functions, but it does not address the development and/or severity of pathological pain syndromes. Similarly, the animal studies that evaluated the effect of PEG in models of SCI focused on the recovery of motor and sensory functions in general, they did not address the occurrence of pathological pain syndromes after injury (Borgens et al., 2002; Layerty et al., 2004). In the contrary, within their particular experimental setting, a strong response (including aggressive behavioral) to light touch, sharp pinch and/or forceful squeezing of the back on the animal, limbs or digit of the paws was considered as a positive response such as the strongest response was given the highest recovery score. In these conditions, it would have been impossible to differentiate between recovery of normal sensory functions and development of abnormal/pathological pain syndromes.

As described earlier, patients with neuropathic pain from a broad range of etiologies are affected by chronic allodynia and hyperalgesia. Recently, specific scoring systems have been developed and applied in clinical setting to monitor changes in sensitivity to painful (hyperalgesia) or normally nonpainful (allodynia) stimuli. These Quantitative Sensory Tests (QST) are becoming a method of choice in assessing evoked pain in patients with neuropathic pain syndromes. QST have been utilized to test various drugs for patients who developed chronic pain symptoms following insults to central and/or peripheral neuronal components including spinal cord injury and stroke (Attal et al., 2002; Attal et al., 2000), surgeries or other invasive treatments, injuries such as bone fractures, shingles and development of postherapeutic neuralgia (Leung et al., 2001), phantom limb pain and idiopathic neuropathy (Attal et al., 1998). Scoring systems to monitor allodynia and hyperalgesia in animal models of peripheral injury or inflammation have been used extensively to study the mechanisms involved in chronic pain development and to test potential treatments. More recently, similar scoring systems have been applied to pain syndromes that can be developed after injury to the central nervous system (Gris et al., 2004; Hao et al., 2004). Similar scoring system are also used to measure pain in acute animal models of inflammation.

Bioactive Agents

Suitable examples of antioxidants include, without limitation, free radical scavengers and chelators enzymes, co-enzymes, spin-trap agents, ion and metal chelators, lipid peroxidation inhibitors such as flavinoids, N-tert-butyl-alpha-phenylnitrone, NXY-059, Edaravone, glutathione and derivates, and any combinations thereof.

Suitable anti-inflammatory compounds include the compounds of both steroidal and non-steroidal structures.

Suitable non-limiting examples of steroidal anti-inflammatory compounds are corticosteroids such as hydrocortisone, cortisol, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluocinolone, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone. Mixtures of the above steroidal anti-inflammatory compounds can also be used.

Non-limiting example of non-steroidal anti-inflammatory compounds include nabumetone, celecoxib, etodolac, nimesulide, apasone, gold, oxicams, such as piroxicam, isoxicam, meloxicam, tenoxicam, sudoxicam, and CP-14,304; the salicylates, such as aspirin, disalcid, benorylate, trilisate, safapryn, solprin, diflunisal, and fendosal; the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; the fenamates, such as mefenamic, meclofenamic, flufenamic, niflumic, and tolfenamic acids; the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and the pyrazoles, such as phenylbutazone, oxyphenbutazone, feprazone, azapropazone, and trimethazone.

The variety of compounds encompassed by the anti-inflammatory group of agents are well-known to those skilled in the art. For detailed disclosure of the chemical structure, synthesis, side effects, etc. of non-steroidal anti-inflammatory compounds, reference may be had to standard texts, including Anti-inflammatory and Anti-Rheumatic Drugs, K. D. Rainsford, Vol. I-III, CRC Press, Boca Raton, (1985), and Anti-inflammatory Agents, Chemistry and Pharmacology 1, R. A. Scherrer, et al., Academic Press, New York (1974), each incorporated herein by reference.

Mixtures of these non-steroidal anti-inflammatory compounds may also be employed, as well as the pharmologically acceptable salts and esters of these compounds.

In addition, so-called "natural" anti-inflammatory compounds are useful in methods of the disclosed invention. Such compounds may suitably be obtained as an extract by suitable physical and/or chemical isolation from natural sources (e.g., plants, fungi, by-products of microorganisms). Suitable non-limiting examples of such compounds include candelilla wax, alpha bisabolol, aloe vera, Manjistha (extracted from plants in the genus *Rubia*, particularly *Rubia Cordifolia*), and Guggal (extracted from plants in the genus *Commiphora*, particularly *Commiphora Mukul*), kola extract, chamomile, sea whip extract, compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include $C_2$-$C_{24}$ saturated or unsaturated esters of the acids, preferably $C_{10}$-$C_{24}$, more preferably $C_{16}$-$C_{24}$. Specific examples of the foregoing include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, and duodenum 3-succinyloxy-beta-glycyrrhetinate.

Suitable examples of neurotransmitter and receptor modulators include, without limitations, glutamate receptor modulators, adenosine receptor modulators, acetylcholine receptor modulators, adrenaline receptor modulators, noradrenaline receptor modulators epinephrine receptor modulators and norepinephrine receptor modulators, cannabinoid receptors modulators, and any combinations thereof. A person of ordinary skill in the art will appreciate that one of the receptor modulators is a ligand naturally occurring in a subject's body. For example, glutamate receptors modulators include glutamate.

In another embodiment, the at least one bioactive agent is a modulator of glutamate transmission, such as (1S, 2S)-1-(4-hydroxyphenyl)-2-(4-hydroxy-4-phenylpiperidino)-1-propanol (also known as CP-101,606), Riluzole (Rilutek®), Topiramate, Amantadine, Gacyclidine, BAY-38-7271, S-1749, YM872 and RPR117824.

In another embodiment, the at least one bioactive agent is a cannabinoid receptor modulator such as dexanabinol (Pharmos Corporation, Iselin, N.J., USA).

Suitable examples of antiplatelet agents include, without limitation aspirin, dipyridamole, ticlopidine and abciximab and any combinations thereof.

Suitable examples of anticoagulant sometime referred to as "blood thinner" agents include, without limitation, heparin and Warfarin (brand name Coumadin®, Warfilone®) and any combinations thereof.

Suitable examples of antineoplastic agents or agents that can interfere with cellular division include, without limitation, vinca alkoloids, vinblastin, vincristine, Palifermin, Paclitaxel, Bleomycin, cytarabine, Vindesine, Pemetrexed, Estramustine, Daunorubicin, and Doxorubicin and any combinations thereof.

Anti-apoptotic agents include, without limitations, inhibitors of pro-apoptotic signals (e.g., caspases, proteases, kinases, death receptors such as CD-095, modulators of cytochrome C release, inhibitors of mitochondrial pore opening and swelling); modulators of cell cycle; anti-apoptotoc compounds (e.g., bcl-2); immunophilins including cyclosporine A, minocycline and Rho kinase modulators, and any combinations thereof. Suitable non-limiting examples of Rho pathway modulators include Cethrin, which is a modified bacterial C3 exoenzyme (available from BioAxone Therapeutics, Inc., Saint-Lauren, Quebec, Canada) and hexahydro-1-(5-isoquinolinylsulfonyl)-1H-1,4-diasepine (also known as Fasudil, available from Asahi Kasei Corp., Tokio, Japan).

Nootropic and growth agents include, without limitation, growth factors; inosine, creatine, choline, CDP-choline, IGF, GDNF, AIT-082, erythropoietin, Fujimycin (IUPAC name [3S-[3R*[E(1S*,3S*,4S*)],4S*,5R*, 8S*,9E,12R*,14R*, 15S*,16R*,18S*,19S*,26aR*]]-5,6,8,11,12,13,14,15,16,17, 18,19,24,25,26,26a-hexadecahydro-5,19-dihydroxy-3-[2-(4-hydroxy-3-methoxycyclohexyl)-1-methylethenyl]-14,16-dimethoxy-4,10,12,18-tetramethyl-8-(2-propenyl)-15,19-epoxy-3H-pyrido[2,1-c][1,4]oxaazacyclotricosine-1,7,20,21 (4H,23H)-tetrone, monohydrate, also known as FK-506 and any combinations thereof.

Suitable non-limiting examples of modulators of lipid formation, storage, and release pathways are apolipoprotein; statins; and any combinations thereof.

Suitable non-limiting of blood flow modulators are adenosine receptor modulators such as ATL-146e.

In different embodiments of the invention, the at least one bioactive agent is selected from the group consisting of thalidomide, bevacizumab, marimastat, α-IFN, MMP inhibitors, Neovastat (AE-941) Rh endostatin, netrins, NOGO-derived proteins, myelin-derived proteins, oligodendrocytes-derived proteins, botulinum toxin, anesthetics, Substance P receptor (NK1) antagonists, opioids, α-Adrenoceptor agonists, cannabinoids, cholinergic receptor agonists, GABA agonists, glutamate receptor antagonists, [N-(4-Hydroxy-3-methoxyphenyl)methyl]-5Z,8Z,11Z,14Z-eicosatetraenamide] (Arvanil), 8-Methyl-N-vanillyl-trans-6-nonenamide (Capsaicin), N-[2-(4-Chlorophenyl)ethyl]-1,3,4,5-tetrahydro-7,8-dihydroxy-2H-2-benzazepine-2-carbothioamide (Capsazepine), 8-Methyl-N-vanillylnonanamide (Dihydrocapsaicin), 6,7-Deepoxy-6,7-didehydro-5-deoxy-21-dephenyl-21-(phenylmethyl)-daphnetoxin, 20-(4-hydroxy-5-iodo-3-methoxybenzeneacetate) (5'-Iodoresiniferatoxin); (+)-Isovelleral, N-Vannilyloleoylamide (Olvanil), Phorbol 12,13-dinonanoate 20-homovanillate, Resiniferatoxin; N-(3-Methoxyphenyl)-4-chlorocinnamide (SB-366791), 2,3,4-Trihydroxy-6-methyl-5-[(2E,6E)-3,7,11-trimethyl-2,6,10-dodecatrienyl]benzaldehyde (Scutigeral), 6,7-Deepoxy-6,7-didehydro-5-deoxy-21-dephenyl-21-(phenylmethyl)-20-(4-hydroxybenzeneacetate)daphnetoxin (Tinyatoxin), capsaicin synthetics, capsaicin derivatives, antibodies targeting vanilloid receptors, capsaicin, capsaicin derivatives, capsaicin synthetics, piperine, mustard oil, eugenol, NGF antagonists, anecortave acetate, triamcinolone acetonide, combretastatin, an anti-angiogenic steroid, an angiostatic steroid, pegaptanib, ranibizumab, minocyclin, fluorocitrate and any combination thereof.

Vascular Indications

Certain aspects of the present invention provide for treatment of vascular indications, such as for example, hypotension, atherosclerotic lesions, vulnerable plaque, and acute myocardial infarct.

Inflammation is now known to be a major driving force underlying the initiation of coronary plaques leading among others, to injured, dysfunctional and leaky endothelium at the area of the lesion. One aspect of the present invention provides for biosealing of the atherosclerotic lesions. This aspect of the present invention may also provides for a combination of a biosealing agent and anti-inflammatory agent.

Exemplary pro-inflammatory molecules include cytokines, chemokines, neuropeptides, bradykinin, histamine and prostaglandins. Suitable active ingredients may include steroids, nonsteroidal anti-inflammatory drugs, COX inhibitors, modulators of TNF-alpha or IL-1 cytokine levels or receptors.

In addition, potential benefit may arise from biosealing protection from oxidized-lipids deposition at the vessel wall/plaques area.

Vulnerable plaque (advanced and rapture prone atherosclerotic lesions and ruptured plaques) are characterized by denuded endothelium with inflammatory elements as a nidus for platelet-fibrin clumping. One aspect of the present invention provides for biosealing of the plaque area to reduce thrombogenicity (platelets deposition).

Myocardial damage after Acute myocardial infarction ("aMI") occurs at large due to the myocardial ischemia reperfusion (IR) injury. This injury is attributed to the extensive cell death within the myocardial tissue, most likely via activation of programmed cell death related among other parameters to oxidative stress due to reperfusion. One aspect of the present invention provides for biosealing during and after aMI to reduce injury and oxidation related damage.

In humans and in animal models, spine injuries especially at high thoracic and cervical levels often result in hypotension which reduces tissue perfusion and may impair functional recovery and orthostatic tolerance. Hypotension can be evaluated by the measure of the mean arterial pressure at rest.

Autonomic dysreflexia is a common and potentially life threatening condition associated with spine injury. Autonomic dysreflexia is a sympathetic reflex characterized by large increases in blood pressure in response to a noxious stimulus below the level of injury; most commonly bladder or bowel distension. It can be evaluated by recording changes in the mean arterial pressure and blood flow during induced episodes of bladder or bowel distension.

Measure of mean blood vessels pressure, blood flow and characteristics of cardiac rhythms can be used to monitor changes in cardiovascular functions.

EXAMPLES

Example 1

Treatment with a Biomembrane Sealing Agent, Polyethylene Glycol or Peg, Reduced the Severity/Occurrence of Chronic Pain Following Tissue Injury Without Affecting Motor Functions or the Size of the Lesion Animal Model of Chronic Pain Wistar female rats weighing 200-250 grams received a controlled clip-compression injury at T4. This experimental model has been previously described in details in Gris et al., 2004. Briefly, animals were premedicated with diazepam (3.5 mg/kg, i.p.) and atropine (0.05 mg/kg, s.c.) in order to facilitate a smooth induction of anesthesia by 4% halothane and maintenance with 1.0-1.5% halothane. The T4 spinal cord segment was exposed by dorsal laminectomy and a modified aneurysm clip, calibrated to 50 grams compression was passed extradurally around the cord and spring released for 60 seconds. Nerve roots were not disrupted during the clip compression.

Treatment

Following injury, animals were placed in their home cage and dosing was initiated. Animals were treated with 0.5% saline or a PEG solution composed of PEG3350 at 30% in 0.5% saline (custom made by AAIPharma Developmental Services, Wilmington, N.C.). Saline and PEG solutions were administered by intravenous injections.

Each animal received 2 injections, the first one 15 minutes after injury and the second injection 6 hours later. Each injection delivered a single dose of 1 g/kg for a total dose of 2 g/kg (body weight). There was 10-11 animals/group. These studies were performed in a randomized and blinded fashion such as the solutions were sent to the Research Center in blindly labeled packages and the code was not revealed to the examiners before the end of the study.

Assessment of Development of Neuropathic Pain

Mechanical Allodynia:

Animals were tested for the development of neuropathic pain or mechanical allodynia before and up to 7 weeks post-injury. Neuropathic pain occurrence and severity was evaluated by the response of the animal to a stimulus that is normally not painful or allodynia. Briefly, a modified Semmes-Weinstein monofilament (Stoelting Co, Wood Dale, Ill.) calibrated to generate a force of 15 mN was applied to the dorsal trunk at dermatomes corresponding to spinal segments immediately rostral to the lesion level (T1-T3). The monofilament was applied 10 times for 3 seconds, with each stimulus being separated by a 5 second interval, and the number of avoidance responses out of a possible 10 were recorded. Avoidance responses were defined as flinching, escape, vocalization, or abnormal aggressive behaviors. The scoring system used to monitor mechanical allodynia has been presented in details in Gris et al., 2004. Mechanical allodynia testing was conducted twice per week and the 2 tests were averaged for each animal and reported as a weekly pain score.

Thermal Hyperalgesia:

Animals were tested for the development of neuropathic pain as measured by thermal hyperalgesia at 7 weeks post-injury. Neuropathic pain occurrence and severity was evaluated by the level of response of the animal to a thermal stimulus that is normally painful. Changes in sensitivity to thermal noxious stimuli were evaluated by inserting the tail of the animal in hot water (50° C.) and by monitoring the time before the tail-withdrawal response (in second).

Assessment of Locomotor Recovery

Locomotor recovery was assessed by the 21-point Basso, Beatie and Bresnahan (BBB) open field locomotor test (Basso et al., 1995), from day 3-21 after injury. Locomotor function was evaluated by 2 blinded investigators at each testing period.

Assessment of Lesion Size

At the end of the behavorial study, animals were anesthetized with a 2:1 ketamine/xylazine solution and perfused with a 4% formaldehyde solution to fix the tissues. Spinal cords were removed, cryostat-sectioned transversely at 20 μm and serially thaw-mounted on slides. One set of cord sections was stained with Solochrome cyanin to detect myelin, and another adjacent set of sections was immunoprocessed for neurofilament 200 in order to identify axons.

Statistical Analysis

To evaluate the significance of difference between experimental groups, data were analyzed using an unpaired, two-tailed t statistical test with confidence intervals of 95%.

Results

Treatment of injured animals with PEG had no effect on lesion size or motor recovery relative to injured animals treated with saline.

Prior to injury, the allodynic pain score of the animals was equal to zero. The number of avoidance responses of the injured animals injected with saline increased progressively after injury to reach a mean pain score of 5+/−0.5 at week-7 post-injury consistent with the development of neuropathic pain. Treatment with PEG significantly (P<0.05) reduced the severity/occurrence of neuropathic pain to 3.5+/−0.5 at week 7. Significant reduction of neuropathic pain (P<0.05) was seen in PEG treated animals as early as week-4 post-injury with a pain score of 2.9+/−0.4 relative to a pain score of 4.5+/0 0.5 in the injured group treated with saline.

In general, non-injured rats have a tail-flick latency response of 10.1±0.7 seconds. At seven weeks post-injury, injured animals treated with saline showed an hyperalgesic response corresponding to tail-flick latency of 3.7+/−0.5 seconds. Hyperalgesia was significantly (p<0.05) reduced in PEG treated animals with an increased latency response of 6.0+/−0.8 seconds relative to the injured group treated with saline.

Example 2

Treatment with a Biomembrane Sealing Agent, Polyethylene Glycol or Peg Reduced Severity of Acute Pain in a Model of Acute Inflammation Induced by a Cuteneous Chemical Irritant Animal Model of Acute Pain and Inflammation The carrageenan model (Iadarola et al., 1988) was used to induce hind paw acute inflammation. Male Sprague-Dawley (258±2.2 g) were anesthetized with isoflurane, and 50 μL of 2% of the chemical irritant λ-carrageenan (w/v; Sigma, catalog #C-3889, lot #122K1444) was injected intradermally into the left hind paw using a 1 cc syringe fitted with a 27 g needle. For the sham group, 50 μL of 0.9% saline was injected into the hind paw in an identical manner.

Treatment

Animals were treated with 0.5% saline or a PEG solution composed of PEG3350 at 30% in 0.5% saline (custom made by AAIPharma Developmental Services, Wilmington, N.C.).

Saline and PEG solutions were administered by intravenous injections. Each animal received 2 injections, the first 15 minutes prior to carrageenan injection and the second one 6 hours after carrageenan injection. Each injection delivered a single dose of 1 g/kg for a total dose of 2 g/kg (body weight). There was 5-6 animals/group. These studies were performed in a randomized and blinded fashion such as the solutions were sent to the Research Center in blindly labeled packages.

Assessment of Pain

Ten hours following carrageenan injection into the left paw, the same paw was tested for mechanical allodynia. Baseline and post-treatment values for non-noxious mechanical sensitivity were evaluated using 8 Semmes-Weinstein filaments (Stoelting, Wood Dale, Ill., USA) with varying stiffness (0.4, 0.7, 1.2, 2.0, 3.6, 5.5, 8.5, and 15 g) according to the up-down method (Chaplan et al., 1994). Animals were placed on a perforated metallic platform and allowed to acclimate to their surroundings for a minimum of 30 minutes before testing.

Assessment of Hind Paw Edema:

Hind paw edema was assessed by measuring paw volume using water displacement. At each test time point, rats were gently restrained, and the hind paws were individually immersed in water up to the hairline above the ankle. The water displaced was measured to the nearest 0.1 ml ($cc^3$). The mean and standard error of the mean (SEM) were determined for each treatment group.

Statistical Analysis:

To evaluate the significance of difference between experimental groups, data were analyzed using an unpaired, two-tailed t statistical test with confidence intervals of 95%.

Results

After 10 hours, the mean pain score in the carrageenan-saline group was 4.2+/−0.6 and significantly lower (p<0.001) than the mean pain score of the sham (saline-saline) animals evaluated at 13.1+/−1.0. In this carrageenan-paradigm, treatment with PEG significantly improved the pain score to 9.9+/−1.1 (p=0.0011) relative to the carrageenan-saline group.

Paw edema or paw volume of the paw that received the carrageenan injection was also decreased by 37% in PEG treated group relative to saline treated animals.

Example 3

Biomembrane Sealing Agent, Polyethylene Glycol, Can Restore Mean Arterial Pressure After Tissue Injury But Did Not Affect Neuronal Control of Autonomic Dysreflexia Animal Model Affected by Decreased Mean Arterial Pressure and Autonomic Dysreflexia Wistar female rats weighing 200-250 grams received a controlled clip-compression injury at T4. This experimental model has been previously described in details in Gris et al., 2004. Briefly, animals were premedicated with diazepam (3.5 mg/kg, i.p.) and atropine (0.05 mg/kg, s.c.) in order to facilitate a smooth induction of anesthesia by 4% halothane and maintenance with 1.0-1.5% halothane. The T4 spinal cord segment was exposed by dorsal laminectomy and a modified aneurysm clip, calibrated to 50 grams compression was passed extradurally around the cord and spring released for 60 seconds. Nerve roots were not disrupted during the clip compression.

Treatment

Following SCI, animals were placed in their home cage and dosing was initiated. Animals were treated with 0.5% saline or a PEG solution composed of PEG3350 at 30% in 0.5% saline (custom made by AAIPharma Developmental Services, Wilmington, N.C.). Saline and PEG solutions were administered by intravenous injections.

Each animal received 2 injections, the first one 15 minutes after injury and the second injection 6 hours later. Each injection delivered a single dose of 0.3 g/kg for a total dose of 0.6 g/kg (body weight). There was 10-11 animals/group. These studies were performed in a randomized and blinded fashion such as the solutions were sent to the Research Center in blindly labeled packages and the code was not revealed to the examiners before the end of the study.

Assessment of Cardiovascular Functions

Mean arterial pressure value at rest and variation of mean arterial pressure during assessment of autonomic dysreflexia were acquired and analysed using Powerlab software (AD Instruments, Mountain View, Calif.). Autonomic dysreflexia is a sympathetic reflex characterized by large increases in blood pressure in response to a noxious stimulus below the level of injury; most commonly bladder or bowel distension. At 6-7 week post-injury the left carotid artery of each animal was cannulated under halothane anesthesia. The severity of autonomic dysreflexia was then tested in each rat approximately 2 or 3 days after cannulation by measuring the increase in mean arterial pressure (MAP) during colon distension with a balloon-tipped catheter inflated with 2.5 ml of air (Weaver et al., 2001). Blood pressure was continuously monitored until a true resting baseline was established, and then the balloon was inflated over 15 sec, with the inflation maintained for 1 min. The MAP was averaged over the entire minute of inflation to determine the dysreflexic response, and two trials were conducted for each animal and averaged. The inflation of the balloon with 2.5 ml of air generates a colon distension similar to that during the passing of a large fecal bolus and is only slightly noxious to a rat with an intact spinal cord (Marsh et al., 2004).

Results

Tissue injuries such as high thoracic and cervical spinal cord injury often result in hypotension. At 7 weeks post-injury, animals treated PEG showed a significant increase (P<0.05) in resting mean arterial pressure with an average value of 115.0+/−3.6 relative to 105.9+/−1.0 mmHg measured in injured animals treated with saline. However, neuronal functions responsible for regulation of autonomic dysreflexia was not affected treatment with PEG suggesting that the biomembrane sealing agent may have had a direct effect on restoring the integrity of blood vessels following tissue injury rather than a general effect on neuronal activity.

Example 4

Biomembrane Sealing Agent, Polyethylene Glycol, Accumulates in and Around Damaged Blood Vessels Animal Model of Tissue Injury and Biodistribution of Active Biomembrane Sealing Agent Male Sprague Dawley rats underwent a moderate T9/10 contusion (1.5 mm displacement) using the Ohio State University Impactor. Immediately after injury, the jugular vein was exposed, and 500 mg (250 mg/ml solution) of biotinylated PEG3000 (Biotin-PEG, custom made By Necktar Therapeutics, Huntsville, Ala.) was injected into the vein. The animals were then sacrificed 24 hours post-injury, and a 1.5 cm segment of spinal cord harvested freshly (ie. no fixation). The cord was cut longiditudinally, and immunohistochemistry was performed using an antibody to rat endothelial cell antigen (RECA-1) to visualize the blood vessels; Cy3 conjugated streptavidin was used to visualize the biotin-labeled PEG.

Results

The analysis of this spinal cord revealed a preferential accumulation of the biomembrane sealing agent at the site of injury. Super-imposed images showed co-localization of the biomembrane sealing agent and endothelial cell signals. In most cases, the biomembrane sealing agent appeared to surround the damaged blood vessels found in the injury site.

CONCLUSION

In the present invention, applicants described the ability of a class of agent, referred to as biomembrane sealing agents, to reduce acute pain and inflammation as well as the development of chronic pain following tissue injury. Applicants demonstrated the ability of this class of agents referred to as "biomembrane" to reduce the severity of hyperalgesia and allodynia following tissue injury. The dramatic reduction of chronic pain development after neuronal injury was not associated with significant changes in motor recovery or size of the lesion. These results emphasize the delineation between recovery of neuronal function in general and development of a pathological condition such as chronic pain. Applicants also showed the ability of the biomembrane sealing agent to accumulate all around damaged blood vessels and help restoring normal mean arterial pressure and blood flow in injured animals.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

What is claimed:

1. A method of treating vascular disease selected from the set consisting of hypotension, atherosclerotic lesions, vulnerable plaque, and acute myocardial infarction, the method comprising delivering by injection to a subject in need thereof a therapeutically effective amount of at least one biomembrane sealing agent and at least one bioactive agent, wherein the at least one biomembrane sealing agent and the at least one bioactive agent is delivered in an injectable composition to an area of the subject affected by vascular disease, wherein further the at least one biomembrane sealing agent is poly(ethylene glycol) with a molecular weight of between 1400 and 20000 Da and comprises more than 10% of the injectable composition, and the at least one bioactive agent comprises at least one neurotransmitter and receptor modulator, anti-inflammatory agent, antioxidant, anti-apoptotic agent, antiplatelet agent, anticoagulant agent, antineoplastic agent, agent that interferes with cellular division, nootropic and growth agent, modulator of lipid formation and transport, blood flow modulator or any combinations thereof, and wherein the injectable composition is incapable of forming a gel.

2. The method of claim 1 wherein the therapeutically effective amount of at least one biomembrane sealing agent is delivered by a method selected from the group consisting of a parenteral administration, an intravenous administration, a perivascular administration, a transvascular administration, a direct application or deposition onto or adjacent to a site of the pathological condition, localized delivery utilizing a catheter, and any combinations thereof.

3. The method of claim 1, wherein the injectable composition is delivered by a localized delivery utilizing a catheter.

4. The method of claim 1, wherein the injectable composition is delivered by an intravenous administration.

5. The method of claim 1, wherein the vascular disease comprises damaged blood vessels.

6. The method of claim 1, wherein the poly(ethylene glycol) comprises PEG 3350, which comprises 30% of the injectable composition.

7. The method of claim 1, wherein the poly(ethylene glycol) comprises PEG 3350, which comprises 30% of the injectable composition and the composition comprises an antioxidant.

8. The method of claim 1, wherein the vascular disease is hypotension.

9. The method of claim 1, wherein the vascular disease is atherosclerotic lesions.

10. The method of claim 1, wherein the vascular disease is vulnerable plaque.

11. The method of claim 1, wherein the vascular disease is acute myocardial infarction.

12. A method of treating vascular disease selected from the set consisting of hypotension, atherosclerotic lesions, vulnerable plaque, and acute myocardial infarction, the method comprising systemically delivering by injection to a subject in need thereof a therapeutically effective amount of at least one biomembrane sealing agent and a therapeutically effective amount of at least one bioactive agent, wherein the at least one biomembrane sealing agent and the at least one bioactive agent are delivered in an injectable composition to an area of the subject affected by vascular disease, wherein further the at least one biomembrane sealing agent is poly(ethylene glycol) and comprises more than 10% of the injectable composition.

13. The method of claim 12, wherein the at least one bioactive agent comprises one or more active ingredients selected from the group consisting of neurotransmitter and receptor modulators, anti-inflammatory agents, antioxidants, anti-apoptotic agents, antiplatelet and anticoagulant agents, nootropic and growth agents; modulators of lipid formation and transport, blood flow modulators and any combinations thereof.

14. The method of claim 12 wherein the therapeutically effective amount of at least one biomembrane sealing agent and the therapeutically effective amount of at least one bioactive agent are delivered by a method selected from the group consisting of a parenteral administration, an intravenous administration, a perivascular administration, and a transvascular administration.

15. The method of claim 12, wherein the injectable composition is delivered by a localized delivery utilizing a catheter.

16. The method of claim 12, wherein the injectable composition is delivered by an intravenous administration.

17. The method of claim 12, wherein the vascular disease comprises damaged blood vessels.

18. The method of claim 12, wherein the injectable composition comprises an antioxidant.

19. The method of claim 12, wherein the poly(ethylene glycol) comprises a molecular weight of between 1400 and 20000 Da.

20. The method of claim 17, wherein the injectable composition is delivered by local administration to the damaged blood vessels.

21. The method of claim 20, wherein the injectable composition is delivered utilizing a catheter for local administration to the damaged blood vessels.

22. The method of claim 12, wherein the poly(ethylene glycol) comprises PEG 3350, which comprises 30% of the injectable composition.

23. The method of claim 12, wherein the poly(ethylene glycol) comprises PEG 3350, which comprises 30% of the injectable composition and the composition comprises an antioxidant.

* * * * *